(12) United States Patent
Luo et al.

(10) Patent No.: US 9,621,825 B2
(45) Date of Patent: Apr. 11, 2017

(54) CAMERA SYSTEM WITH MULTIPLE PIXEL ARRAYS ON A CHIP

(71) Applicant: Capso Vision Inc., Saratoga, CA (US)

(72) Inventors: Jiafu Luo, Irvine, CA (US); Kang-Huai Wang, Saratoga, CA (US); Gordon Wilson, San Francisco, CA (US)

(73) Assignee: CAPSOVISION INC, Saratoga, CA (US)

( * ) Notice: Subject to any disclaimer, the term of this patent is extended or adjusted under 35 U.S.C. 154(b) by 1234 days.

(21) Appl. No.: 13/626,168

(22) Filed: Sep. 25, 2012

(65) Prior Publication Data

US 2013/0020470 A1    Jan. 24, 2013

Related U.S. Application Data

(63) Continuation-in-part of application No. 12/323,219, filed on Nov. 25, 2008, now Pat. No. 9,118,850.

(51) Int. Cl.

| | |
|---|---|
| *H04N 7/00* | (2011.01) |
| *H04N 5/341* | (2011.01) |
| *A61B 1/04* | (2006.01) |
| *G02B 13/06* | (2006.01) |
| *H04N 5/232* | (2006.01) |
| *H04N 5/3745* | (2011.01) |
| *H04N 5/378* | (2011.01) |
| *H04N 5/225* | (2006.01) |
| *G02B 27/10* | (2006.01) |
| *G02B 27/12* | (2006.01) |

(52) U.S. Cl.
CPC ............ *H04N 5/3415* (2013.01); *A61B 1/041* (2013.01); *G02B 13/06* (2013.01); *H04N 5/2258* (2013.01); *H04N 5/23238* (2013.01); *H04N 5/378* (2013.01); *H04N 5/3745* (2013.01); *G02B 27/1066* (2013.01); *G02B 27/126* (2013.01)

(58) Field of Classification Search
CPC ......... H04N 5/232; A61B 1/041; G02B 13/06
USPC ..................................................... 348/36
See application file for complete search history.

(56) References Cited

U.S. PATENT DOCUMENTS

| | | | | |
|---|---|---|---|---|
| 5,510,623 A | * | 4/1996 | Sayag | ........ G01T 1/2928 250/208.1 |
| 7,116,352 B2 | * | 10/2006 | Yaron | ........ A61B 1/00193 348/45 |
| 7,144,366 B2 | * | 12/2006 | Takizawa | ........ A61B 1/00036 600/117 |

(Continued)

*Primary Examiner* — Douglas Blair
(74) *Attorney, Agent, or Firm* — Blairtech Solution LLC

(57) ABSTRACT

An integrated circuit for capturing panoramic image is disclosed. The integrated circuit comprises a plurality of pixel arrays fabricated on a common substrate, wherein each pixel array being positioned to capture an image to be projected thereon, and wherein the orientation of each pixel array is rotated to match with the orientation of the image projected thereon. The integrated circuit also includes readout circuits coupled to the pixel arrays for reading electrical signals corresponding to the images captured from the pixel arrays. In one embodiment, the plurality of pixel arrays corresponds to four pixel arrays and the orientation of said each pixel array is substantially 90° apart from a neighboring pixel array. The integrated circuit further comprises a timing and control circuit, wherein the timing and control circuit is for controlling said one or more readout circuits and the plurality of pixel arrays.

21 Claims, 8 Drawing Sheets

(56) References Cited

U.S. PATENT DOCUMENTS

| | | | |
|---|---|---|---|
| 7,199,348 B2* | 4/2007 | Olsen | G02B 3/0062 250/208.1 |
| 7,423,784 B2* | 9/2008 | Tanabe | H04N 1/401 358/461 |
| 7,796,870 B2* | 9/2010 | Wang | A61B 1/00096 396/14 |
| 8,162,821 B2* | 4/2012 | Kawano | A61B 1/00016 128/899 |
| 8,529,441 B2* | 9/2013 | Bandy | A61B 1/041 600/170 |
| 8,773,500 B2* | 7/2014 | Wilson | A61B 1/00096 348/36 |
| 9,118,850 B2* | 8/2015 | Luo | A61B 1/041 |
| 9,161,684 B2* | 10/2015 | Seibel | A61B 1/0008 |
| 2002/0136550 A1* | 9/2002 | Kuwata | G02B 7/36 396/114 |
| 2003/0038983 A1* | 2/2003 | Tanabe | H04N 1/401 358/461 |
| 2003/0117491 A1* | 6/2003 | Avni | A61B 1/041 348/77 |
| 2005/0043586 A1* | 2/2005 | Suzushima | A61B 1/00096 600/160 |
| 2008/0030573 A1* | 2/2008 | Ritchey | H04N 7/18 348/36 |
| 2008/0080028 A1* | 4/2008 | Bakin | G06T 1/0007 358/514 |
| 2008/0258187 A1* | 10/2008 | Ladd | H01L 27/14603 257/292 |
| 2010/0261961 A1* | 10/2010 | Scott | A61B 1/00193 600/111 |
| 2014/0221742 A1* | 8/2014 | Bandy | A61B 1/041 600/109 |

* cited by examiner

CAMERA SYSTEM WITH MULTIPLE PIXEL ARRAYS ON A CHIP

CROSS REFERENCE TO RELATED APPLICATIONS

The present invention is a continuation-in-part of and claims priority to U.S. patent application Ser. No. 12/323,219 entitled "Camera System with Multiple Pixel Arrays on a Chip", filed on Nov. 25, 2008. The U.S. patent application is hereby incorporated by reference in its entirety.

FIELD OF THE INVENTION

The present invention relates to semiconductor integrated circuits (IC). In particular, the present invention relates to image sensing ICs with multiple pixel arrays in a single IC.

BACKGROUND

An optical camera system typically consists of an optical lens or lens system, and a light sensing element. For digital camera systems, the light sensing elements are based on integrated-circuit sensors fabricated through various manufacturing process, such as CMOS (complementary metal-oxide semiconductor) or CCD (charge-coupled device) processes. Such light sensing ICs traditionally have light sensing elements, called pixels, arranged into one-dimensional (one row) or two-dimensional (many rows and columns) arrays. The pixel array is aligned with the image formed by the associated optical lens system and positioned within the focus depth of the optical system. Each pixel provides an electrical output corresponding to the incident light to which the pixel is exposed.

In a typical camera system, an image corresponding to a scene in the field of view is formed on the sensor, and usually one pixel array is used to capture the image. However, in certain applications, there may be a need to capture multiple images corresponding to multiple views of an object or different objects projected onto a single focal plane. Such applications require multiple cameras or a camera system with multiple matching sensor arrays. Each sensor array is configured to match to a particular image formed through a particular optical path. For example, a panoramic imaging system (e.g., the system described in U.S. Pat. No. 7,817,354) uses multiple sensor arrays to provide overlapping fields of view, such that a composite image may encompass a full 360° field of view. The image sensor ICs can be either CCD or CMOS sensors. Each sensor chip comprises a two-dimensional pixel array typically near the center of the sensor chip. In the straightforward approach using multiple cameras or multiple sensor ICs, each sensor chip is fabricated separately and has its own signal processing chain and/or digital image-processing pipeline. In addition, each sensor IC is readout independently using individual readout circuit. The multiple cameras or sensor chips are then aligned and positioned carefully to match with the image-forming lens system. As a result, such a system results in higher power consumption due to duplicate signal chains on each chip. The system is also more complex and bulky due to difficulty in aligning multiple chips. Additionally, the overall die size of the multiple sensor ICs is larger than an integrated solution incorporating multiple sensor arrays and consequently results in higher production cost.

To overcome such issues, it is therefore desirable to develop an integrated sensor IC incorporating multiple image sensing pixel arrays. Furthermore, it is desirable to use technology compatible with existing state-of-the art semiconductor fabrication process in order to save cost. It is also desirable to further combine common circuits or incorporate associated image processing capability to reduce system cost.

BRIEF SUMMARY OF THE INVENTION

An integrated circuit for capturing panoramic image is disclosed. According to embodiments of the present invention, the integrated circuit comprises a plurality of pixel arrays fabricated on a common substrate, wherein each pixel array being positioned to capture an image to be projected thereon, and wherein orientation of said each pixel array is rotated to match with orientation of the image projected thereon. The integrated circuit also includes one or more readout circuits coupled to the plurality of pixel arrays for reading electrical signals from the pixel arrays, wherein the electrical signals represent the images captured at the plurality of pixel arrays coupled to said one or more readout circuits. In one embodiment, the plurality of pixel arrays corresponds to four pixel arrays and the orientation of said each pixel array is substantially 90° apart from a neighboring pixel array. The one or more readout circuits can be formed on the common substrate. Furthermore, the one or more readout circuits can be formed at a central location on the common substrate, and wherein the plurality of pixel arrays are formed at positions along periphery of the readout circuits.

In another embodiment of the present invention, the integrated circuit further comprises a timing and control circuit formed on the common substrate, wherein the timing and control circuit is for controlling said one or more readout circuits and the plurality of pixel arrays. An aspect of the invention is related to the timing and control circuit design. In one embodiment, the timing and control circuit is configured to cause readout in a row-by-row order starting from a pixel row of first pixel array and finishing at a same pixel row of last pixel array to cover all rows of the plurality of pixel arrays, wherein a pixel row of said each pixel array corresponds to a series of pixels running in parallel with an edge of said each pixel array closest to a center of the plurality of pixel arrays. The row-by-row order can be from the first row to the last row. The row-by-row order may also start from a center row toward both sides of the center row. In another embodiment, said one or more readout circuits are configured to cause readout in a row-by-row order starting from a pixel row of first pixel array and finishing at a same pixel row of last pixel array to cover all rows of the plurality of pixel arrays, wherein a pixel row of said each pixel array corresponds to a series of pixel running perpendicular to an edge of said each pixel array closest to a center of the plurality of pixel.

In yet another embodiment of the present invention, an integrated image sensor to be operationally coupled to a plurality of optical components is disclosed. The integrated image sensor comprises a plurality of pixel arrays fabricated on a common substrate, one or more readout circuits coupled to the plurality of pixel arrays for reading electrical signals from the pixel arrays, and a processing circuit for processing the images sensed by the pixel arrays. The orientation of said each pixel array is rotated to match with orientation of the image captured. Each pixel array is positioned to capture an image in a field of view of a corresponding optical component. The plurality of pixel arrays corresponds to four pixel arrays and the orientation of said each pixel array is substantially 90° apart from a neighboring pixel array. The fields of view of the optical components overlap so that a composite field of view comprises a substantially 360° panorama.

DETAILED DESCRIPTION OF THE INVENTION

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Figure 1:
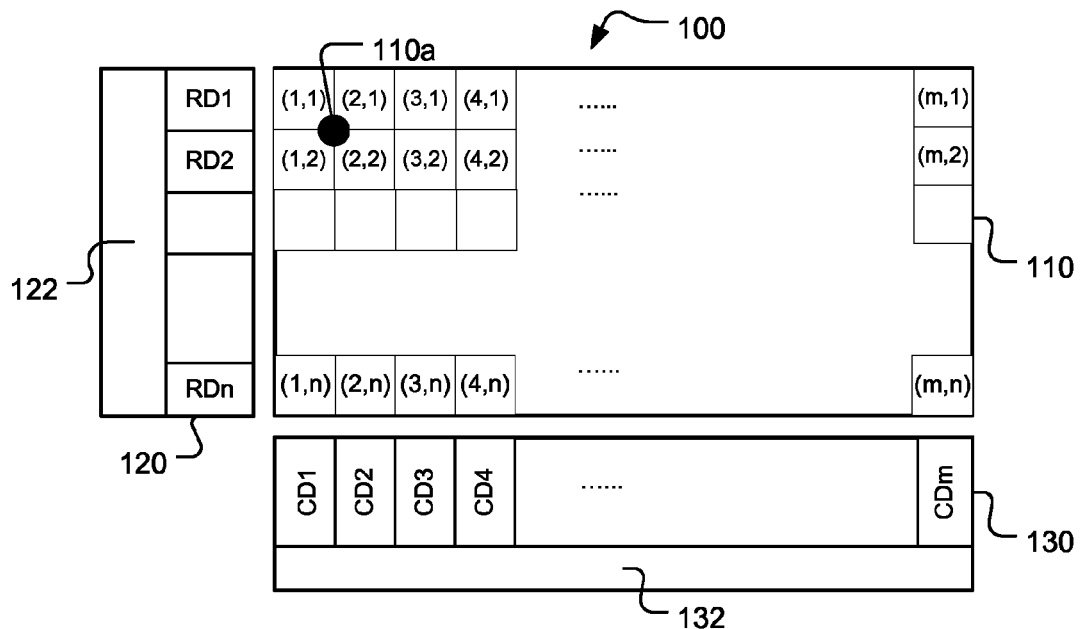
FIG. 1 illustrates an exemplary layout of a conventional two-dimensional pixel array with supporting column and row driving circuits.

A conventional digital camera typically has an optical imaging path with one image sensing IC comprising a two-dimensional (2-D) pixel array. The image sensor is placed at or near the focal plane of the optical imaging path, with the center of the 2-D pixel array aligned with the center of the optical imaging path. FIG. 1 illustrates a typical image sensor 100 including a 2-D pixel array 110, row driver circuit 120 and column driver circuit 130. The 2-D pixel array 100 is configured as two-dimensional sensing elements with n rows and m columns. Each row is substantially the same. If the pixel array is used as a color sensor, color filter with different patterns may be applied on top of the pixel array. The pixel locations of the 2-D array are designated as (x,y), where x represents the horizontal position and y represents the vertical position. The coordinates x and y also represent the column and row numbers of the 2-D pixel array respectively. While FIG. 1 illustrates an example where the pixels in all rows are vertically aligned, some pixel arrays may have offset patterns from row to row. For example, a pixel array may have half-pixel offset for every other rows.

In the horizontal direction, pixels in the same row share common electrical signals provided by row driver 120. Row driver 120 consists of individual row driving circuits RD1, RD2, . . . , RDn for corresponding n rows of the pixel array. In addition to individual row driving circuits, the row driver 120 also includes common components 122 that support all individual row driving circuits. Similarly, pixels in the same column share certain common electrical signals, provided by column circuit 130. Column circuit 130 consists of common components 132 and individual column driving circuits, CD1, CD2, . . . , CDm corresponding m columns of the pixel array. The corner of the pixel array corresponding to the first row and the first column is identified by a black dot 110a.

Figure 2:
FIG. 2 illustrates exemplary timing diagrams to operate a conventional two-dimensional pixel array.

FIG. 2 illustrates exemplary timing diagrams to operate the 2-D pixel array 100 in FIG. 1. To operate the pixel array, the pixel rows are reset before charges are accumulated and read out from the sensing elements. The reset signals 211, 212, 213, . . . , etc. are shown for rows 1, 2, 3, . . . , etc. respectively. Individual row driving circuits generate the respective reset signals 211, 212, 213, . . . , etc. For example, reset signal 211 is generated by the row driving circuit RD1 for the $1^{st}$ row. In the instance as indicated by a short high signal 221 (the reset pulse), the $1^{st}$ row is reset and the row of pixels will start integrating light signals. Individual row driving circuit RD2 for the $2^{nd}$ row generates the timing signal 212, which comprises a reset pulse indicated by 222 to reset the $2^{nd}$ row. The time difference between signal 221 and signal 222 corresponds to one line period. Similarly, timing signal 213 is generated by the individual row driving circuit RD3 for the $3^{rd}$ row and the reset pulse 223 is one line period behind the rest pulse 222. This continues for the remaining rows of the pixel array until the last row is reset. While a pulse signal is illustrated in FIG. 2 to cause a corresponding row to reset, other signal types may also be used. For example, an upward transient signal, such as the leading edge of a positive pulse, or a downward transient signal, such as the trailing edge of a positive pulse may also be used to trigger the reset.

After a period of charge accumulation time, the charge signals can be read out from the pixel array in a row by row fashion. As mentioned before, the sensing elements start to accumulate charges corresponding to the incident light ray after the reset pulse. FIG. 2 illustrates the readout signals generated by the individual driving circuits. For example, individual row driving circuit RD1 for $1^{st}$ row generates a timing signal 231, which comprises a readout pulse 241 to trigger the readout for the $1^{st}$ row. The readout pulse occurs at a desired period of time from the reset pulse 221 for the $1^{st}$ row to integrate charges. The readout pulses 242 and 243 of the readout signal 232 and 233 for the $2^{nd}$ row and the $3^{rd}$ row occur at one row period after respective readout signals 241 and 242. The readout pulses for the remaining rows continue until all rows are read. Again, while a pulse signal is illustrated in FIG. 2 to cause a corresponding row to start the readout, other signal types may also be used. For example, an upward transient signal, such as the leading edge of a positive pulse, or a downward transient signal, such as the trailing edge of a positive pulse may also be used as the readout signal.

The timing scheme shown in FIG. 2 is referred as rolling shutter operation. For video application, the timing signal shown in FIG. 2 repeats frame after frame to form a stream of image frames, which is also referred as a video sequence. As shown in the timing signals of FIG. 2, each row integrates light signal at slightly different time period using the rolling shutter operation. Two neighboring rows have reset time, charge accumulation time and readout time apart by only one line period. However, the time differences between $1^{st}$ and last row are about one frame apart, which may be substantial long. Consequently, the resulting picture with fast moving objects may experience the so-called rolling shutter artifact. One manifest of the rolling shutter artifact is that a vertical line becomes a slant line in the captured picture when the vertical line moves quickly horizontally.

Figure 3:
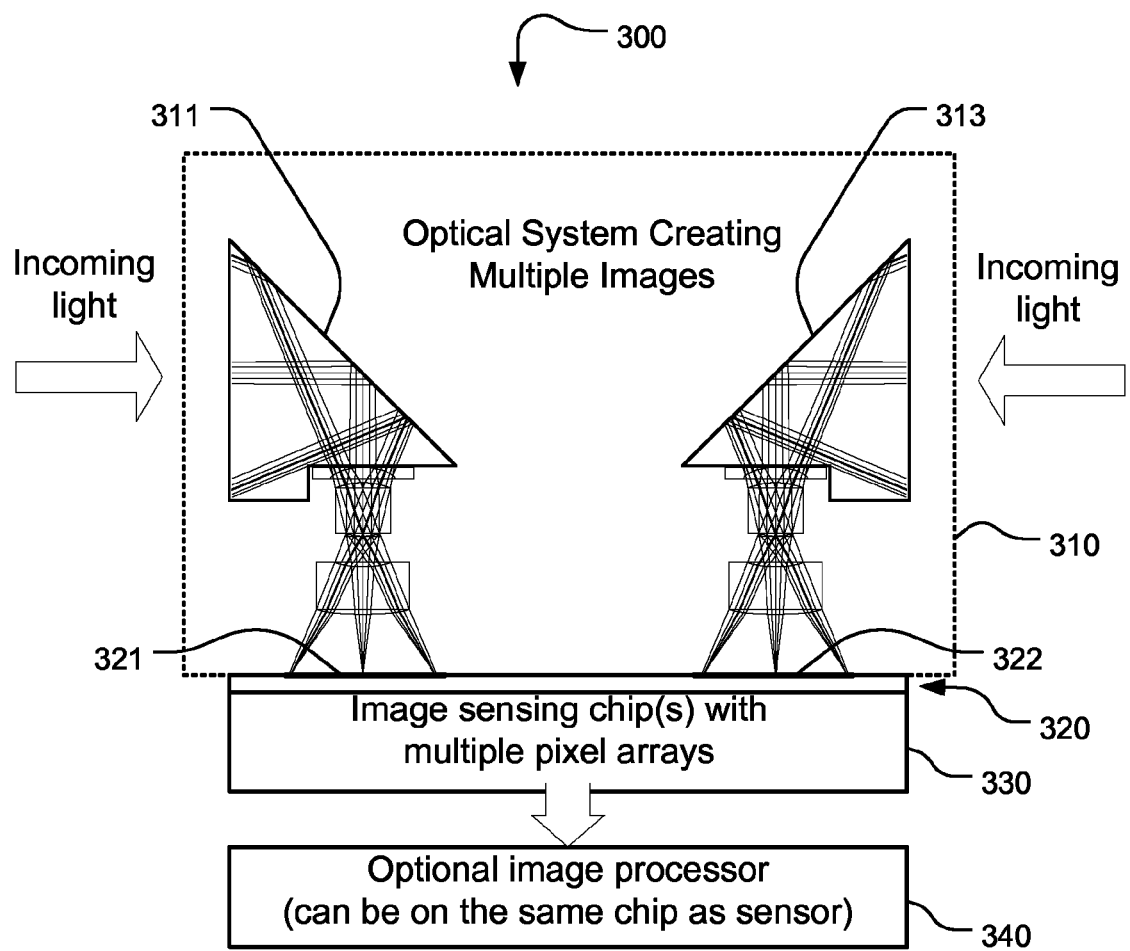
FIG. 3 illustrates a cross-section of an exemplary camera system with four optical sub-systems rotated 90° from each other.

While many cameras have only one optical lens or lens system and require only one 2-D pixel array, there are applications where multiple images are formed as a common focal plane. In these applications, the camera system requires to capture multiple images corresponding to multiple optical paths. FIG. 3 shows the cross-section of an exemplary camera system that is capable of capturing 360° panoramic images. The camera system 300 consists of an optical system 310 with four lens sub-systems. FIG. 3 shows two of the lens sub-systems, 311 and 313, with the optical axes of the objectives oriented 180° apart in object space. The other two lens sub-systems, with optical paths facing back and front, are not shown in the drawing. The lens sub-systems 311 and 313 form images 321 and 322 on a single image plane 320. The other two lens sub-systems also form images on the same image plane 320. Therefore, there are a total of four images projected to the same image plane 320. In practice, images 321 and 322 need not be aligned exactly onto a single image plane and a small difference within the tolerance limit of optical system 310 is allowable. Each of the four images will have a field of view (FOV) corresponding to the FOV of each lens sub-system. The FOV of each lens sub-system is designed to cover a FOV larger than 90°. Accordingly, the four images will be able to cover a total field of view of 360° by properly combining the four images to form a 360° panoramic image.

An image sensing component 330 incorporating an embodiment of the present invention is used to capture the four images corresponding to four optical paths. The images captured are then processed by an image signal processor 340. The image signal processor 340 may share the same substrate as the image sensing component 330. Alternatively, the image signal processor 340 may be implemented separately from the mage signal processor 340. In a conventional approach, the image sensing component 330 would consist of four separate image sensing ICs, where each image sensing IC comprises a 2-D pixel array and associated timing circuits as shown in FIG. 1. In the conventional approach, four individual imaging chips have to be aligned and positioned carefully with the image-forming lens system 310. Therefore, the conventional approach based on multiple imaging chips will result in higher power consumption due to duplicate signal chains on each chip. Furthermore, the conventional approach based on multiple imaging chips is difficult to align and incurs higher production cost.

The image sensing component 330 according to the present invention is implemented as a single image sensing IC. In one embodiment, the image sensing component comprises four pixel arrays fabricated on a common substrate, where the four pixel arrays are configured to capture four corresponding images formed by four respective optical lens sub-systems. Since each optical sub-systems is rotated by 90° from a previous one, the four pixel arrays are also rotated by 90° from each other to match with the orientation of respective images. Compared to a conventional imaging system using multiple image sensor ICs, the present invention provides multitude of advantages. First, there is no need for alignment among individual image sensor ICs on the image plane since only one single image sensor IC is used. In addition, a system incorporating an embodiment of the present invention will result in more compact design, easier fabrication, lower power consumption, and lower manufacturing cost.

Figure 4A:
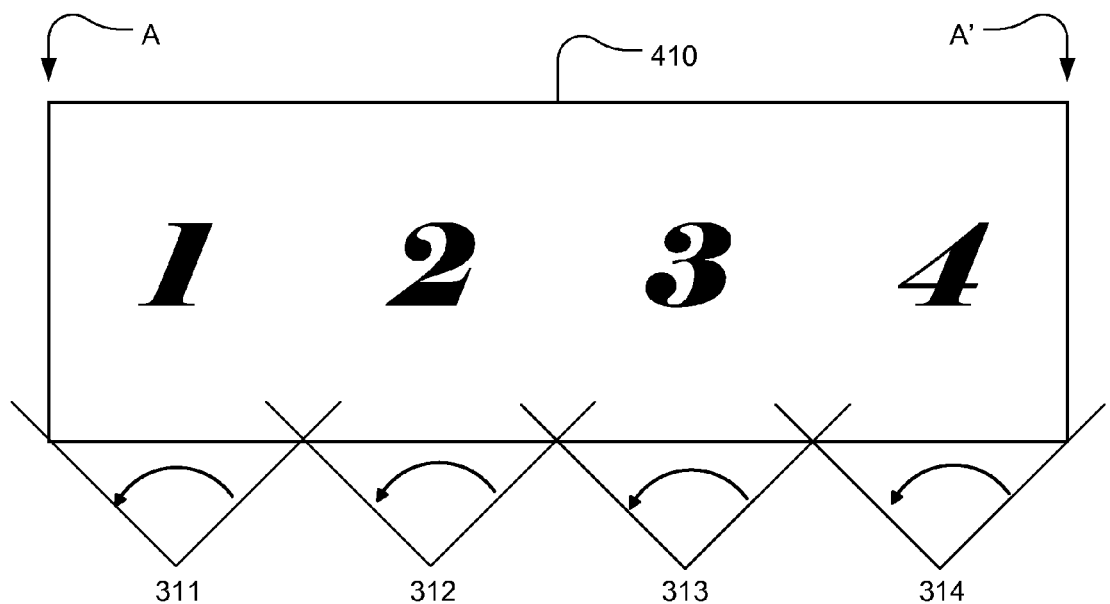
FIGS. 4A-B illustrate an example of panoramic image formation according to the system in FIG. 3.
Figure 4B:
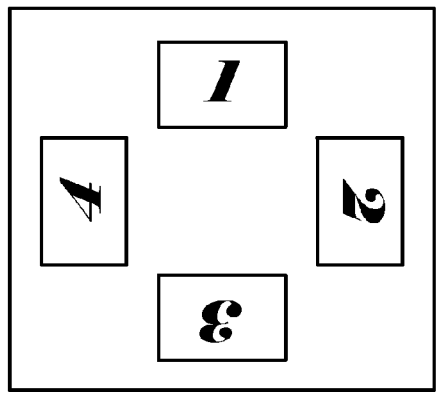

FIG. 4A and FIG. 4B illustrate an example of panoramic image formation using the optical system 310 described in FIG. 3. Picture 410 represents a view inside a circular structure, where edge A and edge A' are connected. Four big letters 1, 2, 3, and 4 are written evenly around the circular wall. If the panoramic camera is placed in the center of the circular structure with the fields of view of the four lens sub-systems aligned with the scene as shown in FIG. 4A, the four images formed on the focal plane are shown in FIG. 4B.

Figure 5:
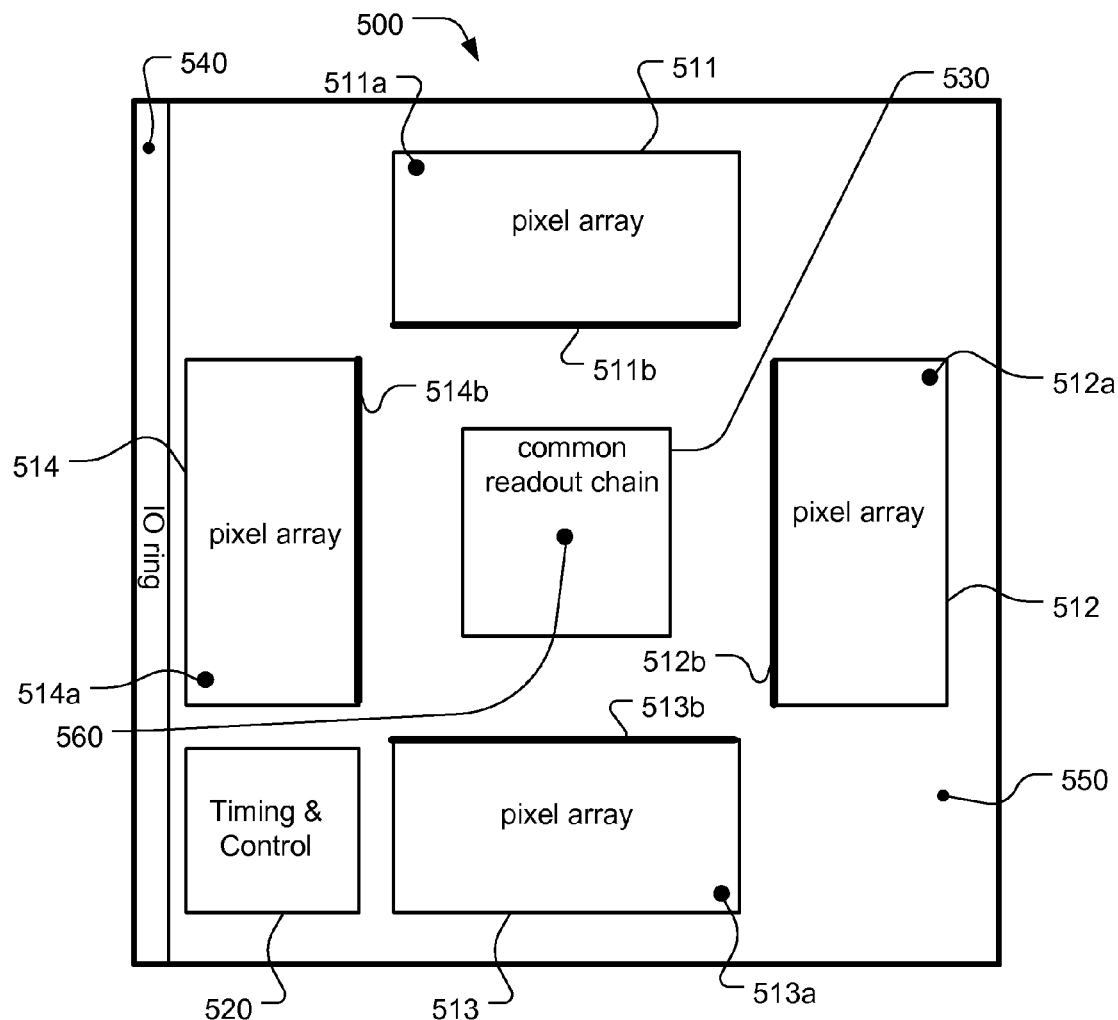
FIG. 5 illustrates an example of an integrated sensor chip having four two-dimensional pixel arrays according to one embodiment of the present invention.

FIG. 5 shows an exemplary layout 500 for an integrated sensing component with multiple pixel arrays according to the present invention to support the four images corresponding to the four optical paths of FIG. 3. The multiple pixel arrays and associated timing/control circuits and common readout chain are implemented on a common substrate 550, such as a semiconductor material. The integrated multiple pixel-array image sensing component comprises separate pixel arrays 511, 512, 513 and 514. In order to properly specify the pixel array orientation, the location of first row and first column of each pixel array is indicated by a black dot (511a, 512a, 513a and 514a). The pixel arrays are configured so that each pixel array is located and oriented properly to capture a corresponding image formed by a lens sub-system. For example, pixel array 514 is provided to capture image 321 that is formed by lens sub-system 311, and pixel array 512 is provided to capture image 322 that is formed by lens sub-system 313. The positions of the multiple pixel arrays are configured to accommodate the positions of the multiple images formed by the optical system. In one embodiment, the optical system forms four images as shown in FIG. 4B. Accordingly, the four corresponding pixel arrays are positioned and oriented symmetrically on a common substrate.

The same pixel array design can be used for all pixel arrays (i.e., pixel arrays 511 to 514). Pixel array 512 can be implemented using the design for pixel array 511 rotated clockwise by 90° as shown in FIG. 5. Similarly, pixel array 513 is rotated clockwise by 90° with respect to pixel array 512 and pixel array 514 is rotated clockwise by 90° with respective to pixel array 513. When the same timing signals are applied to each pixel array (e.g., row by row from row 1 to row n, and along the clockwise direction within each row), the images formed will have correct orientation since the orientations of the pixel arrays in FIG. 5 are aligned with the orientations of the formed images in FIG. 4B. In this case, there is no need for rotating or flipping to correct the image format. The pixel array configuration of FIG. 5 is shown as an example to illustrate how multiple pixel arrays are configured to match with the multiple images formed by multiple optical paths. The pixel arrays are located where the images are to be formed. Furthermore, the pixel array orientation matches with the orientation of the formed image. If the formed images are configured differently, the pixel arrays will have to be configured accordingly.

In order to identify the scanning direction, the center of the four pixel arrays is used as a reference location. For example, the center of the four pixel arrays in FIG. 5 is indicated by the black dot 560. For each pixel array, there is one edge that is closest to the center of the four pixel arrays. For example, edge 511b of pixel array 511 is closest to the center 560. Similarly, edge 512b of pixel array 512, edge 513b of pixel array 513, and edge 514b of pixel array 514 are the edges closest to the center 560. If pixel arrays 511 to 514 use the same scanning order as shown in FIG. 1, the rows of the pixel arrays are parallel to the respective edges closest to the center of the pixel arrays (i.e. center 560). For example, each row of pixel array 511 or 513 runs in horizontal direction and each row of pixel array 512 or 514 runs in vertical direction.

Dedicated row and column driving circuits may be provided for each of these pixel arrays, or centralized driving circuits may be shared by the pixel arrays. When dedicated row and column driving circuits are used, the circuit layout can follow the same rotation as the corresponding pixel array. Accordingly, the same circuit layout for pixel array and driving circuits can be re-used by copying, rotating and placing a common circuit layout. Alternatively, the layout of the four sets of pixel array/driving circuits may be considered jointly to optimize the routing space. For example, if pixel array 511 has a row driving circuit placed to its right hand side, pixel array 512 may place its row driving circuit to its left hand side so that circuit layout of driving circuits for pixel arrays 511 and 512 can be considered jointly to optimize layout efficiency.

Besides pixel arrays 511, 512, 513 and 514, other components may also be formed on substrate 550. For example, timing and control block 520, one or more readout chains (e.g., read out chain 530) for reading out electrical output signals from the pixel arrays, and I/O ring structures 540 can also be formed on the same substrate 550. The readout chain 530 processes the output signals from the pixel arrays before sending out the electrical signal through I/O ring structure 540.

By using 90° rotation, integrated sensor IC layout 500 maintains so-called Manhattan patterns (0° and 90° features) that can be easily manufactured using existing semiconductor fabrication processes, especially during photomask development process. During photomask development processes based on existing technology, a slanted line is represented as zigzags of alternating horizontal and vertical lines, which requires a large amount of data to fiducially represent such a feature. By limiting to 90° rotation, the integrated sensor IC layout 500 is compatible with existing photomask development process. The IC dies in practice always have a rectangular shape that can be diced from a wafer using straight cuts.

Figure 6:
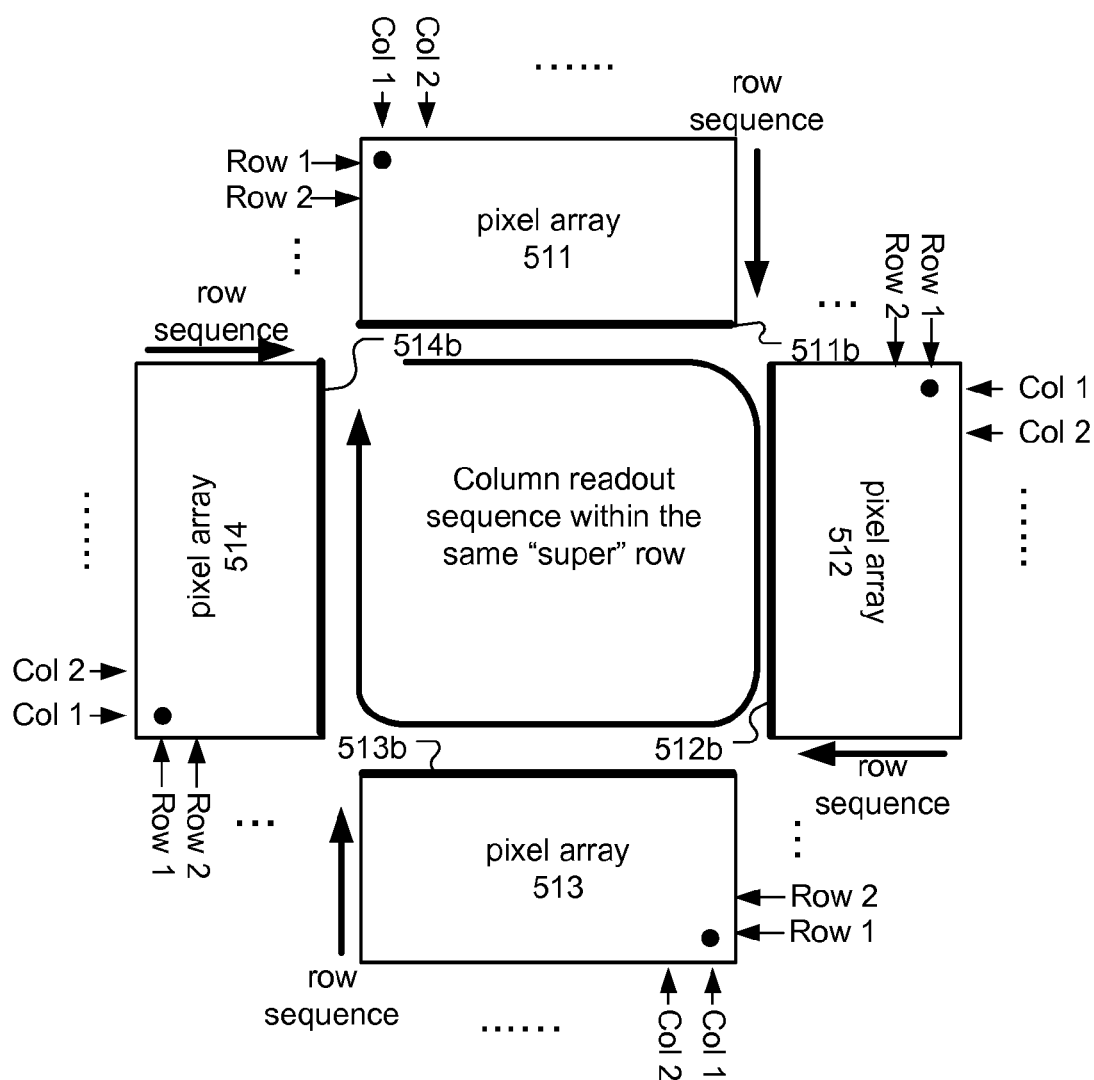
FIG. 6 illustrates an example of the readout sequence of the integrated sensor IC with four pixel arrays according to one embodiment of the present invention, where a super row is read from the four pixel arrays.

The pixel readout directions of these four arrays can be implemented in such a manner that enables easier reconstruction of the four images into a single panoramic image and reduces any potential image artifacts. FIG. 6 illustrates an example of timing signal design for the integrated sensor IC of FIG. 5 according to an embodiment of the present invention. For the four pixel arrays, the locations of the $1^{st}$ row and the $1^{st}$ column are indicated by the black dots 511a, 512a, 513a and 514a. A row of pixels run in parallel with a respective edge (511b, 512b, 513b or 514b) closest to the center of the four pixel arrays. According to one embodiment of the present invention, the readout order across the pixel arrays is as follows. The $1^{st}$ row of each pixel array is read out in the sequential order of pixel arrays 511, 512, 513 and 514. Then the $2^{nd}$ row of each pixel array is read out in the same sequential order. The process continues until all rows are read. Afterward, the process repeats from $1^{st}$ row again. Accordingly, one can think of the combination of $i^{th}$ row of pixel array 511, $i^{th}$ row of pixel array 512, $i^{th}$ row of pixel array 513, and $i^{th}$ row of pixel array 514 form the $i^{th}$ "super" row of the integrated image sensing IC. Within a super row, the pixels will be reading out in a clockwise fashion, starting from pixel array 511 through pixel array 514. The super row is read out one by one from the $1^{st}$ super row to the last super row. Therefore, if each pixel array consists of m columns by n rows, the final combined image will have a size of 4×m columns by n rows.

Figure 7A:
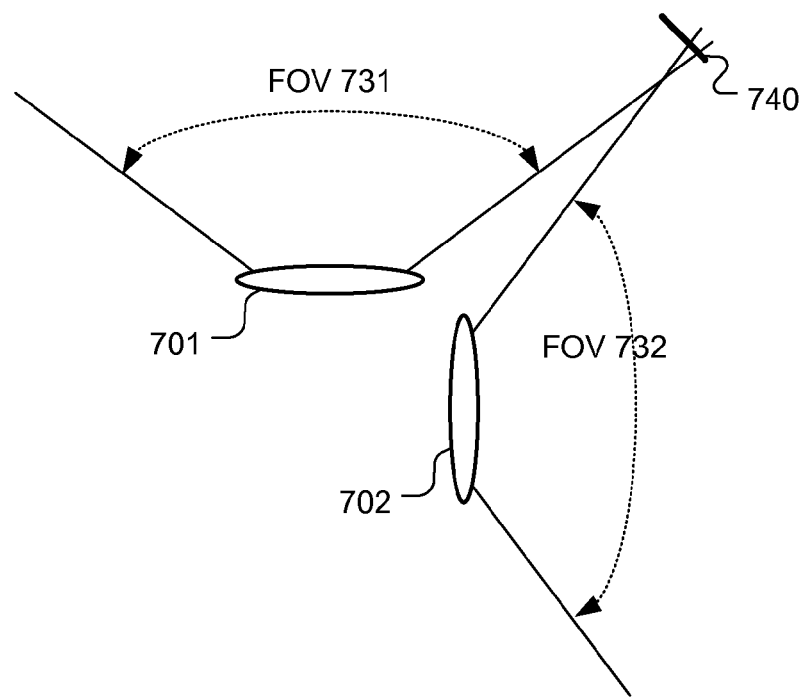
FIG. 7A illustrates the fields of view of two lens sub-systems with an object (letter "F") within the overlapped field-of-view of two neighboring lens sub-systems.

The benefit of the readout sequence as shown in FIG. 6 can be better understood based on the example shown in FIGS. 7A-D. For simplicity, only two neighboring optical sub-systems 701 and 702 are shown. FIG. 7A illustrates a simplified top-view of the two lens sub-systems 701 and 702, where the optical axes are 90° apart in the objective space. Lens sub-system 701 covers a field of view 731 and lens sub-system 702 covers a field of view 732. A letter "F" 740 is mostly within the overlapped region of FOV 731 and FOV 732. Also the letter "F" 740 is partially outside FOV 731 and also partially outside FOV 732. The vertical segment of letter "F" is perpendicular to the cross-section plane.

Figure 7B:
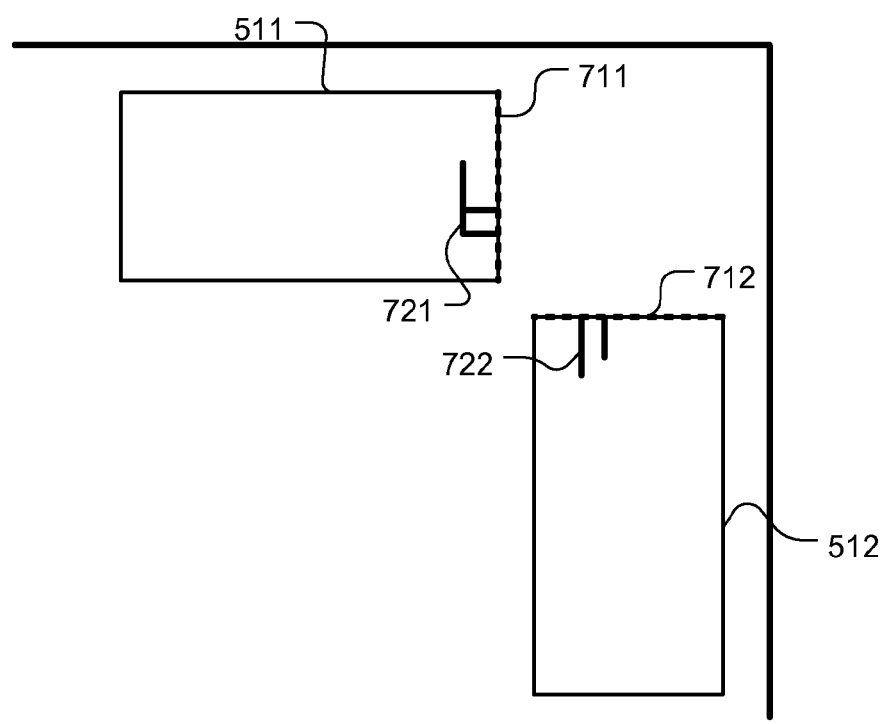
FIG. 7B illustrates the image of the letter "F" in FIG. 7A formed on an image sensing IC having multiple pixel arrays.

FIG. 7B shows the images of the letter "F" 740 on pixel arrays 511 and 512 of the sensing IC 500. Similar to FIG. 7A, only two pixel arrays, 511 and 512, are shown for simplicity. The image formed by lens sub-system 701 is captured by pixel array 511 while the image formed by lens sub-system 702 is captured by pixel array 512. Through lens sub-system 701, the letter "F" forms an image object 721 on pixel array 511. Through lens sub-system 702, the letter "F" forms an image object 722 on pixel array 512. Since part of the letter "F" 740 is outside FOV 731, image object 721 is not a complete picture of letter "F". Similarly, image object 722 is not a complete letter "F" either.

Figure 7C:
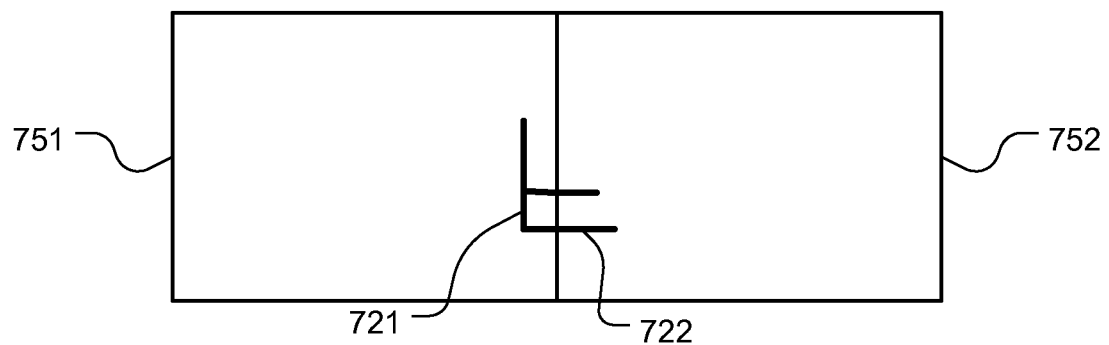
FIG. 7C illustrates the combined image from two neighboring pixel arrays in FIG. 7B, using a readout sequence according to one embodiment of the present invention.

If the readout sequence shown in FIG. 6 is used, each super row is read clockwise and the row-by-row readout order is from respective edges at outside boundaries of the pixel arrays toward the center of the pixel arrays. The combined image by butting neighboring individual images of FIG. 7B is shown in FIG. 7C. Readout of pixel array 511 results in image 751 and readout of pixel array 512 results in image 752. Images object 721 and image object 722 form a complete image of the original letter "F", with a certain amount of overlap. In practice, a certain amount of imperfection due to misalignment between two lens sub-systems may exist. Furthermore, there may be small amount of shift or rotation between two lens sub-systems. Even with such imperfection, the readout sequence described in FIG. 6 will still be able to properly result in two partial image objects corresponding to letter "F". Additional image processing can be developed to identify such overlap and to restore the combined picture.

FIG. 7B illustrates two partial image objects 721 and 722 projected onto two separate pixel arrays by the optical system. The image edges indicated by dashed lines 711 and 712 correspond to the location where neighboring images will be joined to form a panoramic view. The readout sequence as described in FIG. 6 will cause neighboring pixels across image edges 711 and 712 of a same super row to be read out consecutively. Due to the proximity of readout (and reset) time of the two partial images 721 and 722, any image artifact introduced by the rolling shutter operation of FIG. 2 will be minimized.

While FIG. 6 shows a particular readout sequence, alternative readout sequence can be designed so long as it enables easy reconstruction of the combined image and reduces potential imaging artifact. For example, a super row can be read out in a counter-clockwise fashion and start with the first pixel in corresponding row of any pixel array. The super rows can alternatively be readout from a center super row toward two sides of the center super row. In this case, the readout order may finish all super rows on one side of the center super row and then start on the other side. Alternatively, the row-by-row readout order may be alternating between the two sides of the center super row.

Figure 7D:
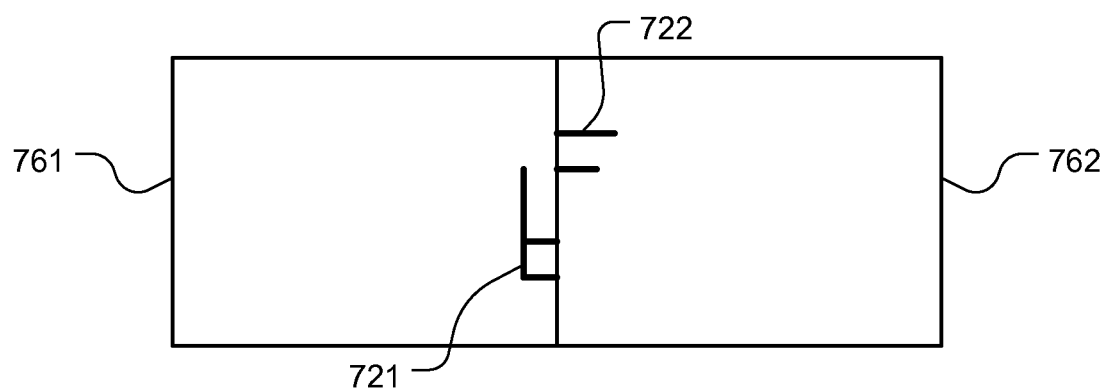
FIG. 7D illustrates the combined image from two neighboring pixel arrays in FIG. 7B, using a readout sequence according to another embodiment of the present invention.

Other readout may also be used and the final image reconstruction may require some processing. FIG. 7D illustrates an alternative readout order. In this example, pixel array 511 in FIG. 7B still uses row by row readout order from chip edges toward the center. This results in an image object 761 in FIG. 7D, which is the same as image 751 in FIG. 7C. On the other hand, pixel array 512 in FIG. 7B uses row by row readout order from the center toward the edges of the IC. This results in an image 762 in FIG. 7D. In order to visualize the image contents of the combined image of FIG. 7D, the sub-image 762 has to be flipped vertically and this implies the need for image processing.

Figure 8:
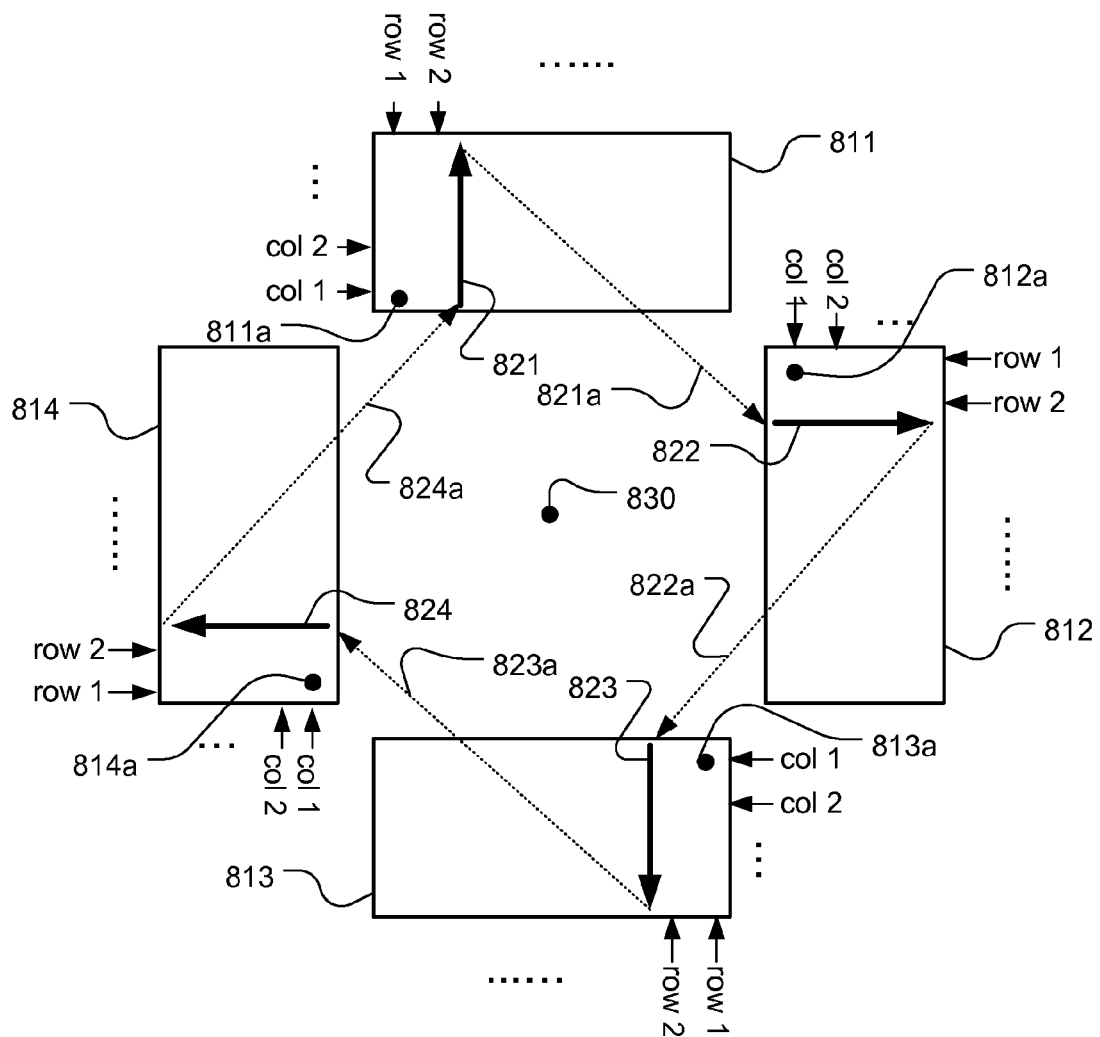
FIG. 8 illustrates an example of the readout sequence of the four pixel arrays according to another embodiment of the present invention.

FIG. 8 shows another example of readout sequence according to another embodiment of the present invention. For each pixel array, the row and column structures are swapped compared to the pixel arrays of FIG. 5. A pixel row corresponds to pixels running along the direction perpendicular to an edge of the pixel array closest to the center of the four pixel arrays. The $1^{st}$ row and $1^{st}$ column locations for each pixel array is indicated by a black dot (811a, 812a, 813a or 814a). The layout of the four pixel arrays 811, 812, 813 and 814 of the image sensing IC is shown in FIG. 8 where each pixel array is rotated clockwise by 90° from the previous one. In other words, each row of pixel array corresponds to a series of pixels running perpendicular to an edge of the corresponding pixel array closest to the center 830 of the four pixel arrays. The readout is in a row-by-row fashion starting from the $1^{st}$ row of pixel array 811. Within each row, the readout order is from a pixel at the edge closest to the center 830 to the opposite edge (i.e., from $1^{st}$ column to the last column). The readout order for the $i^{th}$ rows of the four pixel arrays is illustrated by arrowed lines 821, 822, 823 and 824, where each arrowed line indicates the readout direction of a row from a corresponding pixel array. Dashed lines 821a, 822a, 823a and 824a indicate the readout transition from the $i^{th}$ row of one pixel array to the $i^{th}$ row of the next pixel array. After the $1^{st}$ row of pixel array 811 is read, the readout moves to the $1^{st}$ row of pixel array 812 followed by the $1^{st}$ rows of pixel arrays 813 and 814. After the $1^{st}$ rows of all pixel arrays are read, the $2^{nd}$ rows of all pixel arrays are read. The readout process continues until all rows are read. If pixel array 811 has m rows and n columns, then the combined image will have a size of 4n×m.

The reading sequence according to FIG. 8 may cause an object between the overlapped region of two neighboring pixel arrays to be read out (and reset) at very different times. For example, an object may be partially projected onto the last row of pixel array 811 and the first row of pixel array 812. The corresponding readout times will be about one frame period (i.e. m row periods) apart. This may potentially introduce image artifact. However, if the exposure is controlled so that the exposure is mostly applied during charge integration time, the image readout for the object in the overlapped area will not vary noticeably even though the readout times may be substantially apart. This can be accomplished using strobe control, where flash light timing is synchronized to the timing signal for the pixel arrays. The readout sequence according to FIG. 8 will result in a combined image to be read out in an interleaved fashion and a frame buffer is needed to rearrange the pixel data.

For a pixel array, the readout circuit is usually shared among the rows of the pixel array. The buffer size of the readout circuit is related to the number of columns. Very often, the pixel array has a different number of columns from the number of rows, and there are more pixels in one direction than the other. For example, pixel array 511 of FIG. 5 and pixel array 811 of FIG. 8 have more pixels in the horizontal direction than the vertical direction. In this case, the readout sequence shown in FIG. 8 will result in a shorter bus that couples to all respective column circuits. This will reduce parasitic resistance and capacitance. For the integrated four pixel arrays in a single sensing chip, the "super" row will have even more pixels in each row and cause much more parasitic resistance and capacitance. Therefore, the embodiment as shown in FIG. 8 has the benefit of lower parasitic resistance and capacitance.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. An integrated circuit, comprising:
   a plurality of pixel arrays fabricated on a common substrate, wherein each pixel array comprising a set of pixel rows is positioned to capture an image to be projected thereon, and wherein position of each set of pixel rows is rotated with respect to each other set about a center of the plurality of pixel arrays to match with location of the image projected thereon and the plurality of pixel arrays is designated from a first pixel array to a last pixel array; and
   one or more readout circuits coupled to the plurality of pixel arrays for reading electrical signals from the pixel arrays, wherein the electrical signals represent the images captured at the plurality of pixel arrays coupled to said one or more readout circuits.

2. The integrated circuit of claim 1, wherein the plurality of pixel arrays corresponds to four pixel arrays and the position of each set of pixel rows of the four pixel arrays is rotated substantially 90° from a neighboring set of pixel rows of the four pixel arrays.

3. The integrated circuit of claim 1, wherein said one or more readout circuits are formed on the common substrate.

4. The integrated circuit of claim 3, wherein said one or more readout circuits are formed at a central location on the common substrate, and wherein the plurality of pixel arrays are formed at positions along periphery of the readout circuits.

5. The integrated circuit of claim 3, wherein a timing and control circuit for controlling said one or more readout circuits and the plurality of pixel arrays is formed on the common substrate.

6. The integrated circuit of claim 5, wherein the timing and control circuit causes readout in a row-by-row order starting from a pixel row of the first pixel array and finishing at a same pixel row of the last pixel array to cover all rows of the plurality of pixel arrays, wherein a pixel row of each set of pixel rows corresponds to a series of pixels running in parallel with an edge of each set of pixel rows closest to a center of the plurality of pixel arrays.

7. The integrated circuit of claim 6, wherein said one or more readout circuits cause the readout in the row-by-row order starting from a first pixel row of the first pixel array and finishing at the first pixel row of the last pixel array, and the row-by-row order goes to next pixel row until all pixel rows of the plurality of pixel arrays are read.

8. The integrated circuit of claim 6, wherein said one or more readout circuits cause the readout in the row-by-row order starting from a center pixel row of the first pixel array and finishing at the center pixel row of the last pixel array, and the row-by-row order goes to next pixel row toward two sides of the center pixel row alternately until all pixel rows of the plurality of pixel arrays are read.

9. The integrated circuit of claim 5, wherein the timing and control circuit causes readout in a row-by-row order starting from a pixel row of the first pixel array and finishing at a same pixel row of the last pixel array to cover all pixel rows of the plurality of pixel arrays, wherein a pixel row of each set of pixel rows corresponds to a series of pixel running perpendicular to an edge of each set of pixel rows closest to a center of the plurality of pixel arrays.

10. The integrated circuit of claim 9, wherein said one or more readout circuits cause the readout in the row-by-row order to start from a first pixel row of the first pixel array to the first pixel row of the last pixel array and the row-by-row order goes to next pixel row until aid all pixel rows of the plurality of pixel arrays are read.

11. The integrated circuit of claim 9, wherein said one or more readout circuits cause the readout in the row-by-row order starting from a center pixel row of the first pixel array and finishing at the center pixel row of the last pixel array, and the row-by-row order goes to next pixel row toward two sides of the center pixel row alternately until all rows are read.

12. The integrated circuit of claim 1, wherein the common substrate comprises a semiconductor substrate.

13. The integrated circuit of claim 12, further comprising a processing circuit formed on the common substrate for processing the images sensed by the pixel arrays.

14. The integrated circuit of claim 12, wherein the pixel array corresponds to a CCD sensor or a CMOS sensor.

15. An integrated image sensor to be operationally coupled to a plurality of optical components, comprising:
a plurality of pixel arrays fabricated on a common substrate, each pixel array comprising a set of pixel rows is positioned to capture an image in a field of view of a corresponding optical component, wherein position of each set of pixel rows is rotated with respect to each other about a center of the plurality of pixel arrays to match with location of the image captured and the plurality of pixel arrays is designated from a first pixel array to a last pixel array;
one or more readout circuits coupled to the plurality of pixel arrays for reading electrical signals from the pixel arrays, wherein the electrical signals represent the images captured at the plurality of pixel arrays coupled to said one or more readout circuits; and
a processing circuit for processing the images sensed by the pixel arrays.

16. The integrated image sensor of claim 15, wherein the plurality of pixel arrays corresponds to four pixel arrays and the position of each set of pixel rows of the four pixel arrays is rotated substantially 90° from a neighboring pixel array of the four pixel arrays.

17. The integrated image sensor of claim 16, wherein the fields of view of the optical components overlap so that a composite field of view substantially comprises a 360° panorama.

18. The integrated image sensor of claim 15, wherein said one or more readout circuits are formed on the common substrate.

19. The integrated image sensor of claim 15, wherein said one or more readout circuits are formed at a central location on the common substrate, and wherein the plurality of pixel arrays are formed at positions along periphery of the readout circuits.

20. The integrated image sensor of claim 15, wherein the processing circuit is formed on the common substrate.

21. The integrated image sensor of claim 15, wherein the common substrate comprises a semiconductor substrate.

* * * * *